United States Patent

Katz et al.

[11] Patent Number: 5,549,646
[45] Date of Patent: Aug. 27, 1996

[54] PERIODIC ELECTRICAL LEAD INTERGRITY TESTING SYSTEM AND METHOD FOR IMPLANTABLE CARDIAC STIMULATING DEVICES

[75] Inventors: Samuel M. Katz; Harold C. Schloss, both of Los Angeles, Calif.

[73] Assignee: Pacesetter, Inc., Sylmar, Calif.

[21] Appl. No.: 349,862

[22] Filed: Dec. 6, 1994

[51] Int. Cl.$^6$ .................................................. A61N 1/39
[52] U.S. Cl. ........................................ 607/8; 607/4; 607/5
[58] Field of Search .......................................... 607/4, 5, 8

[56] References Cited

U.S. PATENT DOCUMENTS

| | | | |
|---|---|---|---|
| 4,140,131 | 2/1979 | Dutcher et al. | 607/29 |
| 4,630,615 | 12/1986 | Yomtov | 128/734 |
| 4,776,338 | 10/1988 | Lekholm et al. | 607/24 |
| 4,785,812 | 11/1988 | Pihl et al. | 128/419 D |
| 4,830,006 | 5/1989 | Haluska et al. | 607/4 |
| 4,870,341 | 9/1989 | Pihl et al. | 324/57 R |
| 4,899,750 | 2/1990 | Ekwall | 128/419 PG |
| 5,097,830 | 3/1992 | Eikefjord et al. | 607/8 |
| 5,137,021 | 8/1992 | Wayne et al. | 128/419 PT |
| 5,201,865 | 4/1993 | Kuehn et al. | 28/419 PT |
| 5,215,081 | 6/1993 | Ostroff | 128/419 D |
| 5,224,475 | 7/1993 | Berg et al. | 607/8 |
| 5,233,986 | 8/1993 | Robson | 607/4 |
| 5,285,779 | 2/1994 | Cameron et al. | 607/5 |

FOREIGN PATENT DOCUMENTS 9427674  12/1994  WIPO ........................ 607/5

Primary Examiner—William E. Kamm
Assistant Examiner—Carl H. Layno
Attorney, Agent, or Firm—Harold C. Schloss

[57] ABSTRACT

A periodic electrical lead integrity testing system is provided which periodically tests electrical leads used with an implantable cardiac stimulating device. The system is especially advantageous in multi-functional implantable cardiac stimulating devices. Lead integrity is evaluated by periodically comparing the impedance of the electrical leads to a reference impedance. A pass/fail algorithm is used to determine if electrical lead integrity has been compromised. The system improves the efficacy and safety of implantable cardiac stimulating devices by detecting electrical failures independent of the delivery of therapeutic shocks. The required circuitry adds only minimal complexity and cost to the implantable cardiac stimulating device.

79 Claims, 3 Drawing Sheets

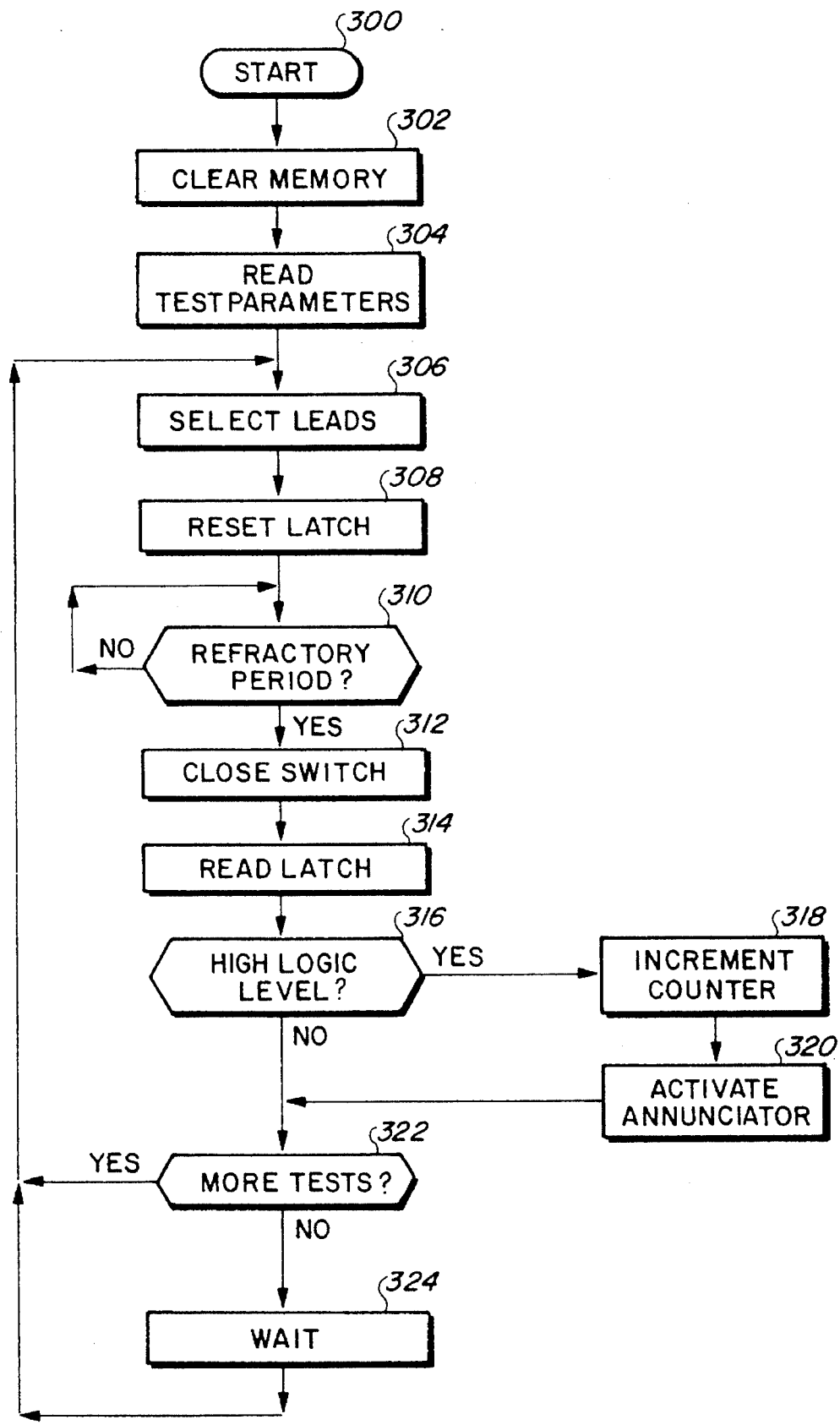

PERIODIC ELECTRICAL LEAD INTERGRITY TESTING SYSTEM AND METHOD FOR IMPLANTABLE CARDIAC STIMULATING DEVICES

BACKGROUND OF THE INVENTION

The present invention relates to implantable cardiac stimulating devices that provide shock therapy for interrupting cardiac arrhythmias. More particularly, the present invention relates to an improved cardiac stimulating device that includes a system for periodically testing the integrity of electrical leads used to deliver therapeutic shocks to cardiac tissue.

One form of cardiac arrhythmia with serious consequences is ventricular tachycardia (VT). VT is a condition where an abnormally high ventricular heart rate severely affects the ability of the heart to pump blood. VT may result in a loss of consciousness due to a decrease in cardiac output. Sustained episodes of VT are particularly dangerous because they may deteriorate into ventricular fibrillation (VF).

VF is the result of rapid and disordered stimulation of the ventricular myocardium, which prevents the ventricles from contracting in a coordinated fashion. VF is the most life-threatening cardiac arrhythmia—unless cardiac output is quickly restored, the patient may suffer severe physiological consequences, including death.

An increasingly common procedure for treating recurrent VT and VF is to implant a small cardiac stimulating device into the body of the patient. These devices automatically detect episodes of VT and VF and administer therapeutic shocks to cardiac tissue in an attempt to revert the arrhythmias. Cardioversion shocks (typically in the range from about 2 joules to about 5 joules) are often administered to interrupt VT. Defibrillation shocks (typically in the range from about 10 joules to about 30 joules) are administered to revert VF and persistent episodes of VT.

The typical adult sinus rhythm range at rest is between 65 and 85 heart beats per minute (bpm). Generally, rates between 60 and 100 bpm are not a cause for concern. This range is called the sinus rate range. Rates falling outside the sinus rate range are known as arrhythmias. An arrhythmia in which the sinus rate is above 100 bpm is called tachycardia. An arrhythmia in which the sinus rate is below 60 bpm is called bradycardia. Pacing devices can be used to provide artificial cardiac pacing to patients exhibiting bradycardia. However, it is increasingly more common to combine pacing devices with cardioverter/defibrillator devices. This allows a physician to prescribe a single cardiac stimulating device that is capable of administering treatment for all forms of arrhythmias, including tachycardia and fibrillation.

Cardiac stimulating devices deliver electrical pulses through electrical leads connected at or near the patient's heart. The electrical lead system may be prone to degradation that can limit the effectiveness of therapy provided by the implantable cardiac stimulating device. There are several reasons why electrical leads may degrade. For example, electrical leads may bind as they are introduced by a physician into the patient's body, thereby subjecting them to excessive local friction. Also, once implanted, the leads may be subjected to constant pressure and local friction caused by normal bodily movements. If the pressure or friction persists, the lead insulation may deteriorate and the conducting wires may partially or completely fracture. Certain types of damage to these leads may have no initial effect on the operating characteristics of the implantable cardiac stimulating device, and may initially go undetected.

Electrical lead integrity is usually assessed soon after implantation by a radiological examination. However, these examinations may not detect minor damage that later can result in lead degradation. Because of the nature of radiological examinations, it is not practical to frequently examine electrical leads by that method. Electrical testing methods are more commonly used to evaluate lead integrity over the operating lifetime of the implantable cardiac stimulating device.

The impedance of electrical leads used with implantable cardiac stimulating devices typically rises slowly after implantation. The normal impedance of a cardiac defibrillating device lead is approximately 30–55 ohms the time of implantation. Several years after implantation, lead impedance should not be more than 30% greater than the impedance at the time of implantation.

If the lead impedance is uncharacteristically high, a lead fracture is usually indicated. Generally if the lead impedance is above 1,000 ohms, lead fracture is almost certain and if it is above 2,000 ohms, lead fracture is certain. Detecting lead fractures is crucial since lead fractures may prevent delivery of effective therapeutic shocks to cardiac tissue.

Some pacemakers are able to periodically test electrical lead integrity by using frequently delivered pacing pulses as test signals, as described in commonly-assigned U.S. Pat. No. 4,899,750, issued on Feb. 13, 1990, to Christer Ekwall of Spanga, Sweden entitled "Lead Impedance Scanning System For Pacemakers." In a similar manner, electrical lead integrity testing by implantable devices that administer higher-energy therapeutic shocks (i.e., cardioversion and defibrillation shocks) has been accomplished by utilizing lead impedance measurements taken during the most recent shock delivery. These measurements are typically analyzed by a physician at the patient's next follow-up visit after delivery of a shock. However, since higher-energy shocks are much less frequently administered than pacing pulses, lead integrity cannot be evaluated by these devices on a regular basis. Therefore, a significant amount of lead degradation may go unnoticed between therapeutic shocks. If the lead damage that occurs between shocks is too severe, it may prevent the device from reverting the next arrhythmia.

There may also be failures or degradation of a less drastic nature which may be intermittent. Indeed, it is common for electrical problems to start as temporary or intermittent failures. Such failures are virtually impossible to detect when testing is done infrequently.

These problems are compounded when pacemaker and cardioverter/defibrillator capabilities are combined into a single device. The high voltages needed for cardioversion and defibrillation can easily damage or destroy the low voltage circuitry of the device. Thus, the lead integrity testing systems found on the relatively low voltage pacemaker side of the device cannot be easily utilized to test the integrity of leads that are used to deliver high energy shocks because of the potential of harm to the low voltage circuitry from high voltage operations. However, because of the desirability of receiving defibrillation or cardioversion therapy shortly after the onset of the arrhythmia, it is desirable that the leads used to deliver such therapy be physically able to deliver such therapy.

What is needed, therefore, is a system and method for periodically evaluating high voltage electrical lead integrity independent of the delivery of therapeutic shocks. The electrical lead integrity testing system should make data available to the physician at the next follow-up visit regardless of whether a shock had been delivered since the last visit. In addition, because of the desire to administer VT or VF therapy shortly after the onset of an arrhythmia, the electrical lead integrity testing system should be capable of warning the individual that a failure which may prevent delivery of a therapeutic shock has occurred, thus allowing the individual to seek repair of the leads before such a shock is actually needed. Furthermore, the circuitry needed to test the integrity of leads on the cardioverter/defibrillator side of the device must not only be able to withstand such high voltages, but must also guard against the possibility of damage to the low voltage circuitry. Thus, there is a need to electrically isolate the high and low voltage operations of the device while at the same time allowing communication between them. Moreover, it is desirable that the amount of additional hardware added to the device to accomplish both the isolation and high voltage lead integrity testing be minimal because of the limited space available in implantable cardiac stimulating devices.

SUMMARY OF THE INVENTION

This invention provides a system for periodically testing the integrity of electrical leads used with implantable cardiac stimulating devices that deliver therapeutic shocks (such as cardioversion or defibrillation shocks) to cardiac tissue. This invention is particularly advantageous in the context of implantable cardiac stimulating devices that provide multiple forms of therapy. The electrical lead integrity testing system of the present invention detects electrical problems more effectively than known lead integrity testing systems which simply store data collected during the last therapeutic shock delivered for the physician to evaluate at the patient's next follow-up visit.

The electrical lead integrity testing system of the present invention advantageously minimizes the amount of energy consumed for testing purposes. This is accomplished by applying low energy test pulses to the lead system, which have a significantly lower energy content than therapeutic shocks. The lead integrity testing system generates data characterizing the impedance of the lead system as either acceptable or too high, even if a therapeutic shock has not been delivered since the last follow-up visit. In this way, electrical lead fractures can be detected and the patient can be warned prior to delivery of a therapeutic shock.

Moreover, the present invention prevents damage to control and logic circuitry by electrically isolating high voltage operations from low voltage operations. While maintaining electrical isolation between the high and low voltage circuits of the device, the present invention allows data obtained by the lead integrity testing circuitry located within the high voltage circuitry of the device to be communicated to the low voltage control and logic circuitry for analysis and processing. This communication is accomplished without the need to add costly and bulky hardware to existing devices.

In addition, the present invention provides for periodic testing of lead integrity at intervals that can be programmed by the physician. For example, the physician may program the implantable cardiac stimulating device to perform lead integrity tests on a daily basis. When the lead system consists of several leads, the lead integrity testing system can perform a series of tests on selected current paths and directions as deemed appropriate by the physician.

The preferred embodiment of a device that incorporates the present invention includes two functionally discrete circuits. The first circuit contains low voltage circuitry for delivering pacing therapy to alleviate a bradycardia and low voltage control and logic circuitry to provide overall control of the operations of the entire device. The other circuit includes low and high voltage circuitry dedicated to the generation and delivery of high energy charges for cardioversion and defibrillation shocks. The low voltage circuitry is electrically isolated from the high voltage circuitry through the use of an isolation circuit, which preferably is a transformer interface or an optical isolation device.

The low voltage circuitry of a preferred embodiment includes a microprocessor which communicates with a defibrillation shock delivery control circuit and a DC/DC converter control circuit by way of a serial interface. The serial interface also allows the two control circuits to communicate with each other. The DC/DC converter control circuit performs the logic operations necessary to create a high voltage charge which can then be stored in a pair of capacitors. The defibrillation shock delivery control circuitry performs the logic operations necessary for timing the delivery of a defibrillation or cardioversion shock, as well as the waveform of that shock. The defibrillation shock delivery control and the DC/DC converter control communicate with a shock delivery circuit by way of an isolation circuit.

The isolation circuit separates the low voltage circuits of the device (responsible for control and logic operations) from the high voltage circuits of the device (responsible for executing cardioversion/defibrillation control and logic operations). This isolation circuit prevents low voltage logic circuitry from being damaged by the high voltage operations of the device. Electrical isolation of the high and low voltage is provided by, for example, a transformer interface or an optical isolation device.

The shock delivery circuitry executes instructions transmitted by the two control circuits and creates a high voltage charge by exposing two high voltage capacitors in series with each other to high DC voltages produced by a DC/DC converter. The shock delivery circuit serves the added function of informing the defibrillation shock delivery control circuitry via the isolation circuitry that a charge has been generated and is ready to be delivered.

An impedance comparison circuit located within the high voltage circuitry is used to determine the impedance of the leads used to deliver cardioversion and defibrillation shocks. The microprocessor provides information to the shock delivery circuit defining which leads are to be tested. In response, the shock delivery circuit connects the impedance comparison circuit to the selected leads. The impedance comparison circuit then evaluates the impedance of the selected leads to determine whether the impedance is within an acceptable range. The impedance comparison circuit provides a pass/fail result representing whether the impedance is within an acceptable range. These results are sent via the isolation circuit to the microprocessor and logic circuitry. Results indicating that lead integrity has been compromised are stored by the microprocessor in memory for later review by the physician. In response to an indication that lead integrity has been compromised, the microprocessor can be programmed to activate an annunciator to warn the individual that a physician should be contacted immediately. Additionally, the microprocessor may, if desired, prevent the selection of a particular lead which failed a lead integrity test for delivery of a therapeutic shock in the event it is needed before corrective measures have been taken.

In another aspect of the invention, an implantable cardiac stimulating device that includes a periodic electrical lead integrity testing system as described above is provided. Further, a method of periodically testing electrical lead integrity is also provided.

The periodic electrical lead integrity testing system of the present invention provides several advantages over known lead impedance measuring systems used in implantable cardiac stimulating devices that deliver therapeutic shocks. For example, electrical lead integrity is evaluated periodically, regardless of whether a therapeutic shock has been delivered, thereby allowing the patient to immediately seek medical help when lead integrity has been compromised. Also, low energy test pulses are used to test lead integrity in order to conserve energy and avoid discomfort to the patient. Further, the periodic lead integrity testing system is implemented using a pass/fail algorithm, so the required circuitry does not add significant complexity or cost to the implantable cardiac stimulating device. Even further, the present invention allows for testing of the high voltage leads (i.e., cardioversion and defibrillation leads) while maintaining isolation between the high and low voltage circuitry of the device.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 3 is a logic flow diagram of a program executed by the microprocessor shown in FIG. 1, for controlling the periodic electrical lead integrity testing system of the present invention.

DETAILED DESCRIPTION OF THE PREFERRED EMBODIMENTS

Figure 1:
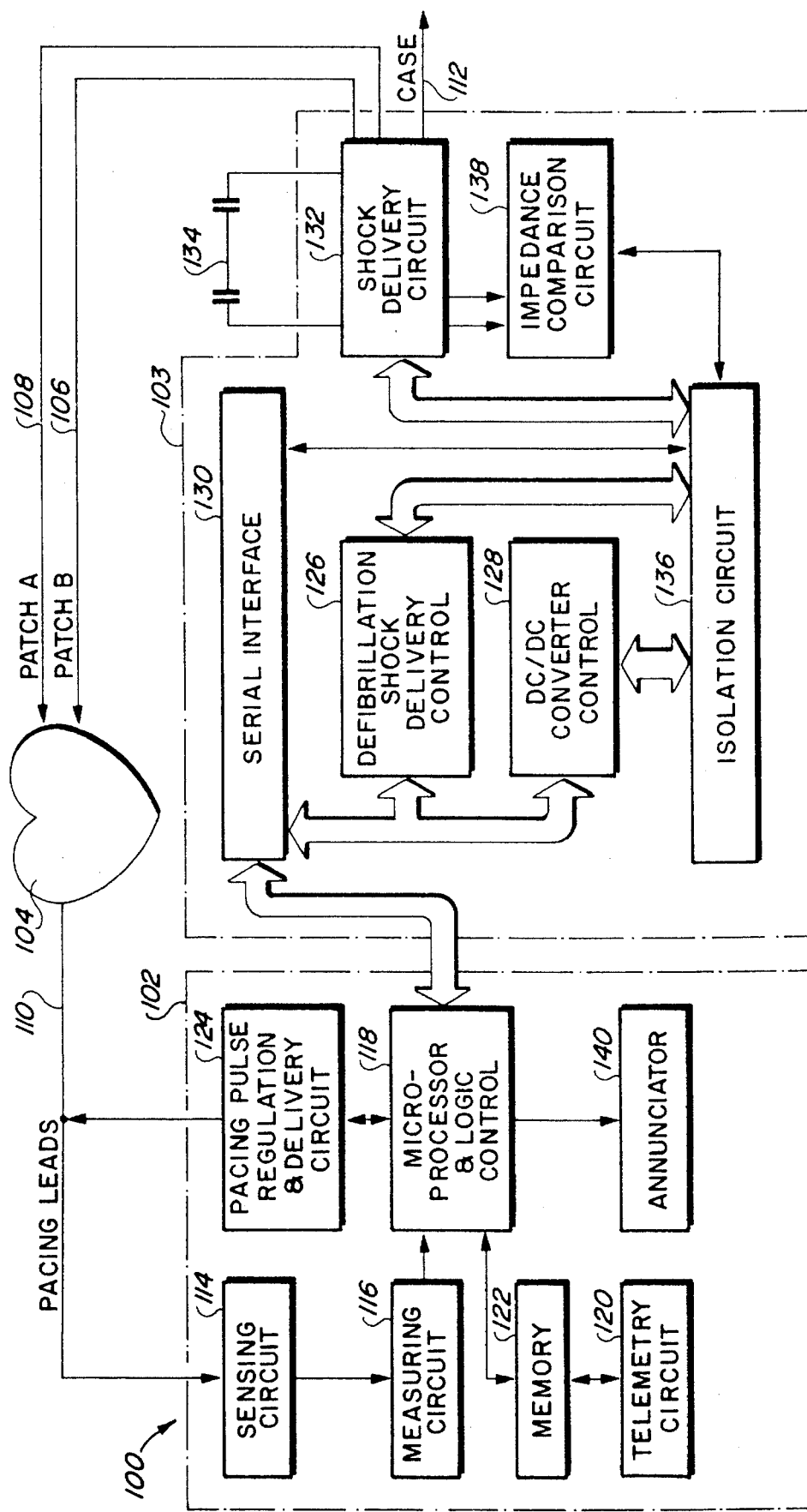
FIG. 1 is a block diagram of an implantable cardiac stimulating device that includes a periodic electrical lead integrity testing system in accordance with the principles of the present invention.

Referring to FIG. 1, a block diagram depicting an implantable cardiac stimulating device 100 in accordance with the principles of the present invention is described. The implantable cardiac stimulating device 100 includes high level logic, control, and communication circuitry 102 which is responsible for overall operational control of the implantable cardiac stimulating device 100. Also included is a circuit 103 dedicated to the control, generation, and delivery of cardioversion and defibrillation therapies.

The implantable cardiac stimulating device 100 administers therapeutic high energy shocks (i.e., cardioversion or defibrillation shocks) or pacing pulses to a patient's heart 104 in order to interrupt cardiac arrhythmias or supply artificial pacing, respectively.

The implantable cardiac stimulating device 100 delivers the therapeutic cardioversion or defibrillation shocks to the patient's heart 104 through a plurality of electrical leads 106 and 108. Low voltage pacing pulses are administered to the patient's heart 104 through a pacing lead system 110. The pacing lead system 110 also serves to sense intrinsic cardiac activity during periods when shock therapy is not being administered.

Although the pacing lead system 110 and electrical leads 106 and 108 are depicted in FIG. 1 as including at least 3 electrical leads, the lead system configuration (i.e., the types and the number of leads) may be varied to meet the needs of a particular patient, and the present invention may be practiced with a variety of lead and electrode configurations which may include patch and spring electrodes, multipolar intravascular catheters, multiple catheters, and catheters in combination with endocardial or extracardial electrodes (not shown). Further, an electrically conductive enclosure 112 of the implantable cardiac stimulating device 100 may be used as an electrode in the delivery of therapeutic shocks. Under these circumstances, the present invention may be used to test the integrity of the implantable enclosure 112 as an electrode.

The pacing lead system 110 conducts analog signals indicative of intrinsic cardiac tissue activity from the patient's heart 104 to a sensing circuit 114. This enables the cardiac stimulating device 100 to monitor the patient's natural cardiac activity. The sensing circuit 114 amplifies and filters the received analog signals. These amplified analog signals are sent to a measuring circuit 116 where the signals are digitized and formatted for use by a microprocessor and logic control circuit 118.

The manner by which the implantable cardiac stimulating device 100 responds to detected arrhythmias may be modified by the physician through an external programming unit (not shown) that communicates with the implantable cardiac stimulating device 100 via a telemetry circuit 120. The telemetry circuit 120 may also be used to deliver pertinent data from the implantable cardiac stimulating device 100 to the external programming unit. Typically, the telemetry circuit 120 transmits data to and from the microprocessor and logic control 118 by way of a memory 122.

The digitized signal transmitted by the measuring circuit 116 is used by the microprocessor and logic control 118 to detect and discriminate among various cardiac arrhythmias (e.g., VT and VF). In response to a detected arrhythmia, the microprocessor and logic control 118 selects which leads 106, 108, or 110 will be used to send an appropriate therapeutic charge. A variety of factors may influence the lead selection made by the microprocessor and logic control 118, including the type and location of the arrhythmia to be treated. The microprocessor and logic control 118 may also select an energy level for the therapeutic shock that is appropriate for the type and severity of the detected arrhythmia. If pacing pulses are needed, for example, to treat a bradycardia, the microprocessor and logic control 118 enables a pacing pulse regulation and delivery circuit 124, which generates and transmits the pulses to the patient's heart 104 at the appropriate times through leads selected by the microprocessor and logic control 118 from the pacing lead system 110. Conversely, if a cardioversion shock or a defibrillation shock is needed, the microprocessor and logic control 118 instructs a defibrillation shock delivery control circuit 126 and a DC/DC converter control circuit 128 to begin preparations to generate and deliver a therapeutic charge. The microprocessor and logic control 118 communicates with the defibrillation shock delivery control circuit 126 and the DC/DC converter control 128 of the circuit 103 through a serial interface 130.

When the microprocessor and logic control 118 issues a command to deliver a cardioversion or defibrillation shock, the DC/DC converter control 128 instructs a shock delivery circuit 132 to begin charging a pair of high voltage capacitors 134 which are connected in series with each other. The instruction signal from the DC/DC converter control 128 is transmitted to the shock delivery circuit 132 by way of an isolation circuit 136. In a preferred embodiment the isolation circuit 136 includes a transformer interface (not shown) which is used to electrically isolate the low voltage control signals transmitted by both the defibrillation shock delivery control circuit 126 and the DC/DC converter control circuit 128 as well as the high level logic, control and communication circuitry 102, from exposure to high voltage. All control or feedback signals passing to or from the shock delivery circuit 132 pass through the isolation circuit 136 in order to prevent damage to the low voltage digital circuits, which may be caused by the high voltage operations.

The shock delivery circuit 132 notifies the defibrillation shock delivery control circuit 126 through the isolation circuit 136 that a sufficient charge has been developed on the capacitors 134. The defibrillation shock delivery control circuit 126 then instructs the shock delivery circuit 132, by way of the isolation circuit 136, to deliver the charge at the appropriate time. It should be noted that the defibrillation shock delivery control circuit 126 works in a similar manner, as do all other elements of the present invention, when delivering cardioversion shocks. The use of the term defibrillation shock delivery control is not intended to mean that only defibrillation shocks are controlled, but includes control of all shocks other than pacing pulses. Based on a determination made by the microprocessor and logic control 118, the appropriate leads 106 and 108 are selected and connected to the high voltage capacitors 134 by the shock delivery circuit 132.

The microprocessor and logic control 118 executes a control program (described in greater detail below) that causes the present invention to perform tests at predetermined time intervals (e.g., daily). Additionally, the physician can initiate electrical lead integrity tests at times other than the preprogrammed time intervals via the telemetry circuit 120.

The present invention tests lead integrity by measuring the impedance of electrical leads selected from the plurality of leads 106 and 108 as well as case 112. When the microprocessor and logic control 118 initiates a test, it communicates with the defibrillation shock delivery control circuit 126, which in turn notifies the shock delivery circuit 132 (through the isolation circuit 136) as to which leads are to be tested. The shock delivery circuit 132 couples the selected leads to an impedance comparison circuit 138. For example, the shock delivery circuit 132 may couple electrical leads 106 and 108 to the impedance comparison circuit 138 to test their integrity. If an indication that lead integrity has been compromised is received, a third electrical lead, for example case 112, can be used with leads 106 and lead 108 sequentially to determine which of the two lead 106 and 108 originally tested is damaged. Any electrical lead or combination of electrical leads can be tested. Preferably, the microprocessor and logic control 118 sequences through a series of tests in order to test the integrity of each electrical lead in accordance with instructions provided telemetrically by the physician.

The total impedance evaluated by the impedance comparison circuit 138 actually consists of several components which must be taken into account when determining if lead integrity has been compromised. For example, if the path consisting of the electrical leads 106 and 108 is being tested, the evaluated impedance includes a transfer impedance through the shock delivery circuit 132, the impedance of the electrical leads 106 and 108, and a lead-tissue interface impedance. The lead-tissue interface impedance includes the impedance of tissue and fluids between the electrical leads 106 and 108, and any interface effects which may be present.

The impedance of properly functioning electrical leads is relatively low, about 30 ohms to about 55 ohms. The transfer impedance through the shock delivery circuit 132 is very low, on the order of several ohms. The lead-tissue interface impedance varies with a multitude of biological factors, but is usually less than about 50 ohms. Accordingly, the total measured impedance should be about 30 ohms to about 100 ohms when the electrical leads are functioning properly.

The change in impedance resulting from lead damage is usually dramatic; therefore, the impedance comparison circuit 138 is preferably designed to implement a pass/fail algorithm. The use of a pass/fail algorithm greatly reduces the complexity and cost of the present invention. If the impedance comparison circuit 138 determines that lead integrity has been compromised, it generates a logic signal that is transmitted to the microprocessor and logic control 118 through the isolation circuit 136. The microprocessor and logic control 118 records the test failure by incrementing a value in the memory 122 at a location that is associated with the electrical lead failing the integrity test.

The present invention preferably further includes an annunciator 140 that, in response to instructions from the microprocessor and logic control 118, alerts the patient when lead integrity has been compromised. The annunciator 140 advantageously alerts the patient regardless of whether a shock had been delivered since the last follow-up visit. Thus, if lead damage occurs between therapeutic shocks, the patient can seek medical attention prior to the delivery of the next shock, thereby reducing the possibility of an ineffective shock. In one embodiment, the annunciator 140 alerts the patient to contact a physician by emitting sound of a particular frequency. In another embodiment, the annunciator 140 generates a low energy shock that is noticeable, but not extremely uncomfortable. In addition, the microprocessor and logic control 118 can be programmed not to select a lead which has been identified as problematic should a therapeutic shock be needed before the patient can seek medical assistance. The physician, using an external programming unit (not shown), can interrogate the memory 122 via the telemetry circuit 120, to evaluate the results of electrical lead integrity tests performed since the last office visit. The physician can then erase the collected data, and even reprogram the testing parameters if so desired. The physician may also run a test at that time, if so desired.

Figure 2:
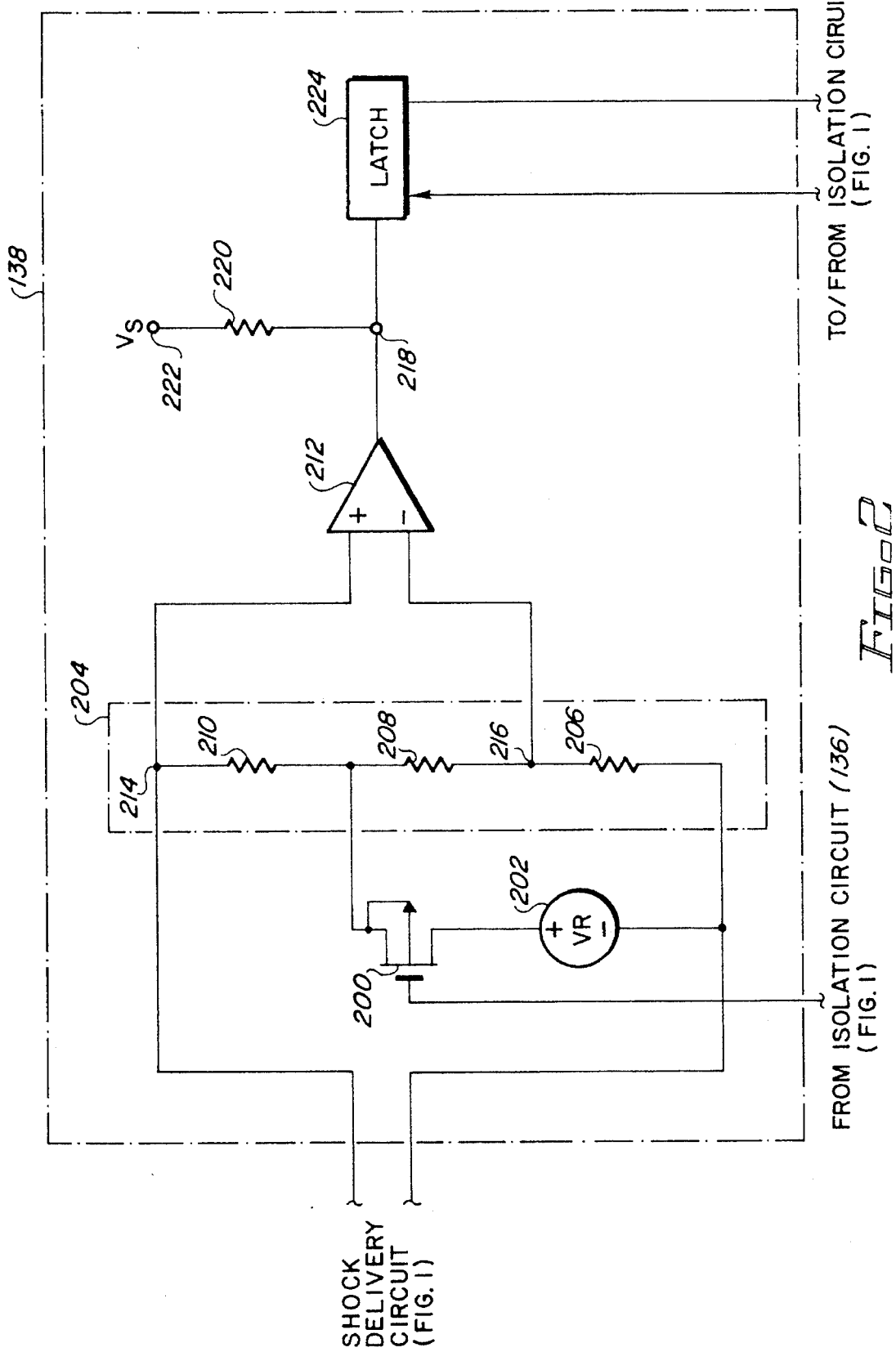
FIG. 2 is a schematic diagram of the impedance comparison circuit of the implantable cardiac stimulating device shown in FIG. 1.

Referring now to FIG. 2, the impedance comparison circuit 138 of FIG. 1 is described in greater detail. One advantage of the present invention is that the circuitry that must be added to the implantable cardiac stimulating device 100 (FIG. 1) to implement periodic electrical lead integrity testing is not costly or overly complex. The impedance comparison circuit 138 includes an electronic switch 200, such as a field-effect transistor (FET) that is responsive to a control signal provided by the microprocessor and logic control 118 (FIG. 1) through the isolation circuit 136 (FIG. 1). Although a FET is preferred, other types of devices may be used as the switch 200. When a FET is used, the drain-source impedance should be accounted for when computing the lead impedance.

When the microprocessor and logic control 118 (FIG. 1) determines that it is time to perform an electrical lead integrity test, it enables the electronic switch 200 so that a reference voltage 202 of about 3.6 volts is applied to a bridge 204. The bridge 204 includes first and second reference resistors 206 and 208, and a series load resistor 210. The series load resistor 210 is connected in series with the load impedance to be measured (i.e., the selected leads) via the shock delivery circuit 132 (FIG. 1). The series load resistor 210 has an impedance of about 200 ohms. In this embodiment, the first and second reference resistors 206 and 208 have impedances equal to the impedance of the series load resistor 210 in conjunction with the drain-source impedance of the switch 200.

A comparator 212 is coupled to the bridge 204, the non-inverting input being connected at a node 214 of the bridge 204 and the inverting input being connected at a node 216 of the bridge 204. An output terminal 218 of the comparator 212 is connected to a pull-up resistor 220. Since the comparator 212 operates as a saturated switch, the impedance of the pull-up resistor 220 is not critical. Typically, the impedance of the pull-up resistor 220 is between a few hundred ohms and a few thousand ohms. A supply voltage 222 defines the "high" logic level and is typically about 3.6 volts.

When the impedance of the electrical leads under test is greater than the impedance of the first and second reference resistors 206 and 208, the comparator 212 generates a "high" logic signal at the output terminal 218. Conversely, the comparator 212 generates a "low" logic signal at the output terminal 218 when the impedance of the first and second reference resistors 206 and 208 is greater than the impedance of the electrical leads under test. The comparator 212 thus performs a straightforward comparison test to determine the integrity of the selected electrical leads.

Over time, the impedance of some or all of the electrical leads may gradually increase without necessarily signifying lead failure. Such uneventful increases in impedance are accommodated by choosing reference resistors that have an impedance of about twice the impedance of a pair of recently implanted leads. When lead integrity has been compromised, the measured impedance of the selected electrical leads is at least an order magnitude greater than the impedance of the first and second reference resistors 206 and 208. In that event, the comparator 212 generates a "high" logic signal at the output terminal 218, as described above. When the reference resistors are selected in this manner, it is not likely that there will be false readings due to multiple transitions around the trigger point of the comparator 212. However, to avoid even the remote possibility of false readings, a Schmitt trigger circuit (not shown) can be utilized.

A latch 224 is coupled to the output terminal 218 of the comparator 212. The latch 224 stores the most recent result of an electrical lead integrity test, which is then communicated to the microprocessor and logic control 118 (FIG. 1) via the isolation circuit 136 (FIG. 1). The result of the test is then stored in the memory 122 (FIG. 1) as described above.

Referring now to FIG. 3, a logic flow diagram representing a control program for the microprocessor and logic control 118 (FIG. 1), as it may be implemented in suitable microcode or any higher level language, is described. The program may be implemented as part of a larger program that controls the other operations of the cardiac stimulating device, with appropriate modifications made as required to support those other operations. The program begins at start 300, which is followed by a step 302 where the microprocessor and logic control 118 (FIG. 1) clears the portion of the memory 122 (FIG. 1) where any previously collected electrical lead integrity test data had been stored.

At a step 304, the microprocessor and logic control 118 (FIG. 1) reads the testing parameters stored in the memory 122 (FIG. 1), which include the period between electrical lead integrity tests and a sequence for selecting the leads to be tested. The time between electrical lead integrity tests may depend on several factors including the type of implantable cardiac stimulating device, the lead system configuration, and the patient's particular physical condition. Frequent testing may reduce the lifetime of the implantable cardiac stimulating device, due to a depletion of energy reserves. A reasonable time between identical electrical lead integrity tests may be about one day. Leads that are subject to persistent friction or pressure may be tested more frequently.

Steps 302 and 304 are performed when the implantable cardiac stimulating device 100 (FIG. 1) is initially implanted or when the test parameters are changed by the physician. This typically occurs at implantation, but may be performed after implantation through instructions communicated via telemetry circuit 120 (FIG. 1).

At a step 306, the microprocessor and logic control 118 (FIG. 1) causes the shock delivery circuit 132 (FIG. 1) to connect a pair of electrical leads selected from leads 106 (FIG. 1), 108 (FIG. 1) or case 112 (FIG. 1) for an electrical lead integrity test in accordance with the testing parameters read at the step 304. At a step 308, the microprocessor and logic control and logic control 118 (FIG. 1) resets the latch 224 (FIG. 2) in preparation for an electrical lead integrity test result.

At a test 310, the microprocessor and logic control 118 (FIG. 1) determines, using the sensed signal indicative of intrinsic cardiac activity, whether the heart is substantially refractory. Although a low energy test pulse is used, under certain circumstances, the application of the reference voltage 202 (FIG. 2) to the heart may interfere with the heart's natural rhythm. Thus, in the preferred embodiment of this invention, the present invention interacts with the sensing functions of the implantable cardiac stimulating device 100 (FIG. 1) so as to synchronize the application of the reference voltage 202 (FIG. 2) to a period of the cardiac cycle when the heart is substantially refractory.

Alternatively, the test voltage can be selected to be below the patient's capture threshold, in which case it would be unnecessary to determine whether the heart is refractory. This alternative is particularly attractive when patch electrodes are used, because more energy is required to capture the heart when patch electrodes are used. Transvenous electrodes require less energy to capture the heart. It is therefore more difficult in a transvenous system to select a test voltage below the capture voltage. However, with careful selection of system components, a sub-capture test voltage can be implemented even in a transvenous system.

If it is determined at test 310 that the heart is not refractory, then the system will wait until the heart becomes refractory. Once the system detects a refractory period, the microprocessor and logic control 118 (FIG. 1) initiates an electrical lead integrity test by simultaneously enabling the FET switch 200 (FIG. 2) and the latch 224 (FIG. 2) at a step 312. This causes the reference voltage 202 (FIG. 2) to be applied to the bridge 204 (FIG. 2). Voltages proportional to the impedance of the first and second reference resistors 206 and 208 (FIG. 2) and the impedance of the selected electrical leads are applied to the comparator 212 (FIG. 2).

At a step 314, the microprocessor and logic control 118 (FIG. 1) reads the result stored in the latch 224 (FIG. 2). At a test 316, the microprocessor and logic control 118 (FIG. 1) determines the logic level of the result read from the latch 224 (FIG. 2). If a logical "low" level is read from the latch 224 (FIG. 2), then the tested electrical leads are functioning properly and no data is stored.

If a logical "high" level is read from the latch 224 (FIG. 2), electrical lead integrity has been compromised. In that event, at a step 318, the microprocessor and logic control 118 (FIG. 1) increments a value in the memory 122 (FIG. 1) at a location associated with the electrical leads selected by the microprocessor and logic control 118 (FIG. 1) in the step 306. Then, at a step 320, the microprocessor and logic control 118 (FIG. 1) causes the annunciator 140 (FIG. 1) to notify the patient that lead integrity has been compromised.

At a test 322 following either the test 316 or the step 320, the microprocessor and logic control 118 (FIG. 1) determines if additional electrical leads are to be selected for testing during the current interval. If additional tests are to be performed, the program loops back to the step 306, at which the microprocessor and logic control 118 (FIG. 1) causes the shock delivery circuit 132 (FIG. 1) to connect the next leads to be tested. If no additional tests are to be performed during the current interval, the program proceeds to a step 324, where the program waits for the current interval to elapse before initiating another series of tests, beginning with the step 306.

At a later time the physician may modify the testing parameters stored in the memory 122 (FIG. 1) using an external programmer via the telemetry circuit 120. (An example of such an external programmer is the APS II model 3003, manufactured and sold by Pacesetter, Inc. of Sylmar, Calif. Descriptions of such external programmers may be found in U.S. Pat. Nos. 4,791,936; 4,809,697; 4,944,299; and 5,309,919, all of which are incorporated herein by reference.) This allows the physician to change the time between electrical lead integrity tests or to change the electrical lead testing sequence. The physician may also use an external programmer to read the test results and clear the portion of the memory 122 that stores the test results.

The ability to modify the testing parameters is important since in the later part of the cardiac stimulating device life cycle, the leads may require more frequent testing. Also, depending on the patient's anatomy and the extent of any initial damage to the leads during implantation, particular electrical leads may deteriorate at a faster rate and require more frequent testing.

Various alternatives may be utilized in addition to the invention as described so far. For example, one testing parameter that might be available for physician control would be to control the pulse width or pulse amplitude of the pulse applied to the electrical leads being tested. Another alternative might be to provide a variable voltage source in place of reference voltage 202 and allow the physician to control the voltage applied across the electrical leads under test. An additional control signal to the variable voltage source would need to be provided from the isolation circuit 136. Combining these two alternatives would allow the physician to control both the pulse width and voltage used during testing of the electrical leads. Additionally, each lead combination to be tested could have an individually programmed pulse width and voltage to be utilized during the test.

The control of the annunciator 140 may be made more sophisticated by providing control logic for it. Thus at step 320 (FIG. 3) the control logic for the annunciator 140 would be activated. This control logic would be connected to memory 122 and would allow selection of frequency of annunciation, and pattern of annunciation. This would allow for use of the annunciator 140 to alert the patient or physician to the specific condition detected by the cardiac stimulation device.

Many physicians choose to program several therapies that are to be attempted in an order selected by the physician, when the device detects that either ventricular fibrillation or ventricular tachycardia has occurred. A physician may have different therapies selected for application when ventricular tachycardia is detected than when ventricular fibrillation is detected. Each therapy would consist of one or more leads and an output pulse to be applied to those leads. The output pulse could be defined in terms of the voltage to be applied, the energy to be applied, the pulse width to be applied, or the current to be applied. The output pulse would be delivered by the shock delivery circuit. The therapies that a physician selects could utilize different lead combinations. An additional feature may be added to the device wherein when a lead is suspected to have failed, the device's control program can alter the sequence or priority of the therapies so as to attempt those therapies that utilize working leads first, and try any therapies utilizing potentially failing leads afterwards.

Thus, a periodic electrical lead integrity testing system is provided. One skilled in the art will appreciate that the present invention can be practiced by other than the described embodiments, which are presented for purposes of illustration and not of limitation, and the present invention is bounded only by the claims that follow.

What is claimed is:

1. An implantable cardiac stimulating device for administering electrical stimulation to cardiac tissue, said cardiac tissue having periods of refractoriness through at least one electrical lead to interrupt cardiac arrhythmias, the implantable cardiac stimulating device comprising:

high voltage shock delivery circuitry, electrically connected to said at least one electrical lead, for generating a high energy shock and for delivering said shock to cardiac tissue through said at least one electrical lead in response to a shock delivery control signal;

low voltage control circuitry for detecting the onset of a cardiac arrhythmia, for generating said shock delivery control signal to cause said high voltage shock delivery circuitry to generate and deliver said high energy shock, and for generating a lead integrity test control signal to initiate a lead integrity test on said at least one lead, said low voltage control circuitry comprising means for delivering said shock delivery control signal to said high voltage shock delivery control circuitry and further comprising means for detecting refractory periods of said cardiac tissue, wherein said low voltage control circuitry initiates lead integrity tests only during said refractory periods; and a lead integrity testing circuit, coupled to said at least one electrical lead via said high voltage shock delivery circuitry and to said low voltage control circuitry, for performing said lead integrity test by evaluating the impedance of said at least one electrical lead in response to said lead integrity test control signal and for providing results of said lead integrity test to said low voltage control circuitry.

2. The implantable cardiac stimulating device of claim 1, wherein said means for delivering said shock delivery control signal comprises isolation circuitry for providing a communication interface between said low voltage control circuitry and said high voltage shock delivery circuitry and said lead integrity testing circuit, wherein said isolation circuitry allows communication of said shock delivery control signal, said lead integrity test control signal and said results of said lead integrity test while protecting said low voltage control circuitry from damage by high voltage operations of said high voltage shock delivery circuitry.

3. The implantable cardiac stimulating device of claim 1, wherein the low voltage control circuitry further comprises a memory circuit for storing said results from said lead integrity test.

4. The implantable cardiac stimulating device of claim 1, wherein the low voltage control circuitry further comprises a telemetry circuit for communicating said results to an external programming unit.

5. The implantable cardiac stimulating device of claim 1, wherein the low voltage control circuitry further comprises an annunicator for alerting a patient when said lead integrity testing circuit determines that lead integrity has been compromised.

6. The implantable cardiac stimulating device of claim 5, wherein the annunciation comprises a pattern of annunciation, and wherein the low voltage control circuitry further comprises control logic means for controlling the pattern of annunciation by said annunciator.

7. The implantable cardiac stimulating device of claim 5, wherein the annunciation comprises a frequency of annunciation, and wherein the low voltage control circuitry further comprises control logic means for controlling the frequency of annunciation by said annunciator.

8. The implantable cardiac stimulating device of claim 1, wherein:

said implantable cardiac stimulating device delivers said electrical stimulation through a plurality of electrical leads;

said low voltage control circuitry generates a lead selection control signal that identifies at least one lead of said plurality of leads to be tested; and said high voltage shock delivery circuitry, in response to said lead selection control signal, couples said identified at least one lead to said lead integrity testing circuit for lead integrity testing and wherein said low voltage control circuitry further comprises means for delivering said lead selection control signal to said high voltage shock delivery control circuitry.

9. The implantable cardiac stimulating device of claim 8, wherein to evaluate the impedances of said plurality of electrical leads, said lead integrity testing circuit applies a low energy test pulse through each of said identified at least one lead in response to said lead integrity test control signal.

10. The implantable cardiac stimulating device of claim 8, wherein said low voltage control circuitry further comprises:

means for selecting a sequence of therapies, wherein each therapy comprises a selection of at least one lead of said plurality of electrical leads; and memory means for storing said selected sequence of therapies.

11. The implantable cardiac stimulating device of claim 10, wherein said low voltage control circuitry further comprises control means for modifying said stored selected sequence of therapies in response to said results from said lead integrity test.

12. The implantable cardiac stimulating device of claim 1, wherein said low voltage control circuitry initiates said lead integrity test independently of delivery of said high energy shock.

13. The implantable cardiac stimulating device of claim 1, wherein to evaluate the impedance of said lead, said lead integrity testing circuit applies a low energy test pulse through said lead in response to said lead integrity test control signal.

14. The implantable cardiac stimulating device of claim 13, wherein said lead integrity testing circuit compares the impedance of said lead to a reference impedance.

15. The implantable cardiac stimulating device of claim 14, wherein said lead integrity testing circuit provides a logic signal to said low voltage control circuitry when lead integrity has been compromised.

16. The implantable cardiac stimulating device of claim 13, wherein said low energy test pulse comprises a pulse width, said implantable cardiac stimulating device further comprising means for selecting the pulse width of said low energy test pulse.

17. The implantable cardiac stimulating device of claim 13, wherein said low energy test pulse comprises a pulse amplitude, said implantable cardiac stimulating device further comprising means for selecting the pulse amplitude of said low energy test pulse.

18. The implantable cardiac stimulating device of claim 17, wherein said low energy test pulse comprises a pulse width, said implantable cardiac stimulating device further comprising means for selecting the pulse width of said low energy test pulse.

19. The implantable cardiac stimulating device of claim 1, wherein said low voltage control circuitry initiates lead integrity tests at predetermined intervals.

20. The implantable cardiac stimulating device of claim 19, further comprising means for selecting said predetermined intervals.

21. An implantable cardiac stimulating device for administering electrical stimulation to cardiac tissue through a plurality of electrical leads to interrupt cardiac arrhythmias, the implantable cardiac stimulating device comprising:

high voltage shock delivery circuitry, electrically connected to said plurality of electrical leads, for generating a high energy shock and for delivering said shock to cardiac tissue through said plurality of electrical leads in response to a shock delivery control signal;

low voltage control circuitry for detecting the onset of a cardiac arrhythmia, for generating said shock delivery control signal to cause said high voltage shock delivery circuitry to generate and deliver said high energy shock, and for generating a lead integrity test control signal to initiate a lead integrity test on at least one of said plurality of electrical leads, said low voltage control circuitry comprising means for delivering said shock delivery control signal and said lead selection control signal to said high voltage shock delivery control circuitry and said low voltage control circuitry generates a lead selection control signal that identifies said at least one of said plurality of electrical leads to be tested; and a lead integrity testing circuit, coupled to said plurality of electrical leads via said high voltage shock delivery circuitry and to said low voltage control circuitry, for performing said lead integrity test by evaluating the impedance of said at least one of said plurality of electrical leads in response to said lead integrity test control signal and for providing results of said lead integrity test to said low voltage control circuitry, wherein said high voltage shock delivery circuitry, in response to said lead selection control signal, couples said identified at least one of said plurality of electrical leads to said lead integrity testing circuit for lead integrity testing, and further wherein to evaluate the impedances of said plurality of electrical leads, said lead integrity testing circuit applies a low energy test pulse through each of said identified at least one of said plurality of electrical leads in response to said lead integrity test control signal and further wherein said lead integrity testing circuit applies a different low energy test pulse through each of said identified at least one of said plurality of electrical leads in response to said lead integrity test control signal.

22. The implantable cardiac stimulating device of claim 21, wherein said low energy test pulse comprises a pulse width, said implantable cardiac stimulating device further comprising means for selecting the pulse width uniquely for the low energy test pulse associated with each electrical lead.

23. The implantable cardiac stimulating device of claim 21, wherein said low energy test pulse comprises a pulse amplitude, said implantable cardiac stimulating device further comprising means for selecting the pulse amplitude uniquely for the low energy test pulse associated with each electrical lead.

24. The implantable cardiac stimulating device of claim 23, wherein said low energy test pulse comprises a pulse width, said implantable cardiac stimulating device further comprising means for selecting the pulse width uniquely for the low energy test pulse associated with each electrical lead.

25. An implantable cardiac stimulating device coupled to a pacing lead system for delivering pacing pulses to cardiac tissue and for sensing signals representative of natural cardiac activity, and coupled to a plurality of high energy shocking leads for delivering high energy shocks to cardiac tissue, comprising:

a pacing and device control circuit comprising:
  pacing pulse regulation and delivery circuitry for generating, in response to pacing pulse control signals, pacing pulses which are delivered to said cardiac tissue through said pacing lead system,
  means for sensing signal representative of natural cardiac activity,
  processing circuitry for amplifying and digitizing said sensed signals, and
  microprocessor and logic control circuitry for analyzing said amplified and digitized signals to detect cardiac arrhythmias, for providing pacing pulse control signals and high energy shock control signals in accordance with said detected arrhythmias, and for providing lead integrity test control signals to initiate lead integrity tests on said plurality of high energy shocking leads; and a high energy shock delivery and control circuit comprising:
  a communication interface coupled to said microprocessor and logic control circuitry of said pacing and device control circuit,
  high voltage shock delivery circuitry, electrically connected to said plurality of high energy shocking leads, for generating, in response to high energy shock generation control signals, high energy shocks which are delivered to cardiac tissue through said plurality of high energy shocking leads;
  high energy shock control circuitry, coupled to said communication interface, for providing said high energy shock generation control signals in response to said high energy shock control signals provided by said microprocessor and logic control circuitry,
  isolation circuitry for providing a communication path between said high voltage shock delivery circuitry and said high energy shock control circuitry and for providing a communication path to said communication interface while protecting said high energy shock control circuitry, said communication interface, and said pacing and device control circuit from high voltage operations of said high voltage shock delivery circuitry, and
  impedance comparison circuitry, directly coupled to said high voltage shock delivery circuitry and coupled to said microprocessor and logic control circuitry through said isolation circuitry and said communication interface, for performing lead integrity tests on said plurality of high energy shocking leads in response to said lead integrity test control signals and for providing results of said lead integrity tests to said microprocessor and logic control circuitry, wherein, to evaluate the impedance of said lead, said impedance comparison circuitry applies at least one low energy test pulse through said plurality of high energy shocking leads in response to said lead integrity test control signals.

26. The implantable cardiac stimulating device of claim 25, wherein said pacing and device control circuit further comprises memory, coupled to said microprocessor and logic control circuitry, for storing results from said lead integrity tests.

27. The implantable cardiac stimulating device of claim 25, wherein said pacing and device control circuit further comprises telemetry circuitry, coupled to said microprocessor and logic control circuitry, for communicating said results to an external programming unit.

28. The implantable cardiac stimulating device of claim 25, wherein said pacing and device control circuit further comprises an annunciator, coupled to said microprocessor and logic control circuit, for alerting a patient when said results indicate that lead integrity has been compromised.

29. The implantable cardiac stimulating device of claim 25, wherein:
  said microprocessor and logic control circuitry generates high energy lead selection signals that identify leads of said plurality of high energy shocking leads to be tested; and
  said microprocessor and logic control communicates said high energy lead selection signals to said high energy shock control circuitry, which in turn communicates said high energy lead selection signals through said isolation circuitry to said high voltage shock delivery circuitry which responsively couples said identified leads to said impedance comparison circuitry for lead integrity testing.

30. The implantable cardiac stimulating device of claim 25, wherein said microprocessor and logic control circuitry initiates said lead integrity tests independently of delivery of said high energy shocks.

31. The implantable cardiac stimulating device of claim 25, wherein said impedance comparison circuitry compares the impedance of said plurality of high energy shocking leads to a reference impedance while said low energy test pulses are being applied.

32. The implantable cardiac stimulating device of claim 31, wherein said impedance comparison circuitry provides a logic signal to said microprocessor and logic control circuitry when the integrity of said plurality of high energy shocking leads has been compromised.

33. The implantable cardiac stimulating device of claim 25, wherein said microprocessor and logic control circuitry initiates lead integrity tests at predetermined intervals.

34. The implantable cardiac stimulating device of claim 25, wherein said impedance comparison circuit comprises:
  a reference voltage supply;
  a reference impedance;
  a switch for coupling said reference voltage supply to said plurality of high energy shocking leads and said reference impedance in response to said lead integrity test control signals;

a comparator for comparing the impedance of said plurality of leads to the impedance of said reference impedance, wherein said comparator provides a logic signal indicating that lead integrity has been compromised when the impedance of said plurality of leads exceeds the impedance of said reference impedance; and a latch for temporarily storing said logic signal for subsequent retrieval by said microprocessor and logic control circuitry.

35. In an implantable cardiac stimulating device detachably coupled to a lead in contact with cardiac tissue, the implantable cardiac stimulating device including:

high voltage shock delivery circuitry, electrically coupled to said lead, for generating high energy shocks and for delivering said high energy shocks to cardiac tissue through said lead, low voltage control circuitry for detecting the onset of cardiac arrhythmias and for causing said high voltage shock delivery circuitry to generate and deliver said high energy shocks in response to a detected cardiac arrhythmias, means for evaluating the integrity of said lead and for generating test results, and means for passing signals between said high voltage shock delivery circuit and said low voltage control circuitry, a method for evaluating the integrity of said lead comprising the steps of:
generating a low energy test pulse with said high voltage shock delivery circuitry;
applying said low energy test pulse to said lead in response to a lead integrity test control signal provided by said low voltage control circuitry;
evaluating the integrity of said lead while said test pulse is being applied;
generating test results indicative of whether lead integrity has been compromised; and
providing said test results to said low voltage control circuitry.

36. The method of claim 35, wherein said providing step comprises providing said test results to said low voltage control circuitry through said means for passing signals, wherein said means for passing signals comprises an isolation circuit which protects said low voltage control circuitry from high voltage operations of said high voltage shock delivery circuitry.

37. The method of claim 35, further comprising the step of storing said test results in a memory.

38. The method claim 35, further comprising the step of using a telemetry circuit to telemetrically communicate said test results to an external programming unit.

39. The method of claim 35, further comprising the step of using an annunciator to alert a patient when said test results indicate that lead integrity has been compromised.

40. The method of claim 35, wherein said applying step comprises applying said low energy test pulse independently of delivery of said high energy shocks.

41. The method of claim 35, wherein said evaluating step comprises the step of comparing the impedance of said lead to a reference impedance.

42. The method of claim 35, wherein said cardiac stimulating device further includes means for detecting refractory periods of said cardiac tissue, the method further comprising the step of:

generating said lead integrity test control signal, said lead integrity test control signal being generated only when a refractory period of said cardiac tissue is detected by said means for detecting refractory periods.

43. An implantable cardiac stimulating device for administering electrical stimulation to cardiac tissue, said cardiac tissue having periods of refractoriness, through at least one lead to interrupt cardiac arrhythmias, the implantable cardiac stimulating device comprising:

shock delivery circuitry, electrically coupled to said at least one lead, for generating a high energy shock and for delivering said high energy shock to cardiac tissue through said at least one lead in response to a shock delivery control signal;

control circuitry for detecting the onset of a cardiac arrhythmia, for generating said shock delivery control signal to cause said shock delivery circuitry to generate and deliver said high energy shock, and for generating a lead integrity test control signal to initiate a lead integrity test on said at least one lead;

a lead integrity testing circuit, coupled to said at least one lead, for performing said lead integrity test in response to said lead integrity test control signal and for providing results of said lead integrity test to said control circuitry, wherein said lead integrity testing circuit performs said lead integrity test by applying a low energy test pulse to said at least one lead and further wherein the result of said lead integrity test comprises a pass/fail indication of the integrity of said at least one lead;

a means for passing signals between said lead integrity testing circuit and said control circuitry; and a means for passing signals between said shock delivery circuit and said control circuitry.

44. The implantable cardiac stimulating device of claim 43, wherein the control circuitry further comprises a memory circuit for storing said results from said lead integrity test.

45. The implantable cardiac stimulating device of claim 43, wherein the control circuitry further comprises a telemetry circuit for communicating said results to an external programming unit.

46. The implantable cardiac stimulating device of claims 43, wherein the control circuitry further comprises an annunciator for alerting a patient when said result of said lead integrity test is a fail indication.

47. The implantable cardiac stimulating device of claim 46, wherein the annunciation comprises a pattern of annunciation, and wherein the control circuitry further comprises control logic means for controlling the pattern of annunciation by said annunciator.

48. The implantable cardiac stimulating device of claim 46, wherein the annunciation comprises a frequency annunciation, and wherein the control circuitry further comprises control logic means for controlling the frequency of annunciation by said annunciator.

49. The implantable cardiac stimulating device of claim 43, wherein:

said implantable cardiac stimulating device delivers said electrical stimulation through a plurality of electrical leads;

said control circuitry generates a lead selection control signal that identifies at least one lead of said plurality of leads to be tested; and said shock delivery circuitry, in response to said lead selection control signal, couples said identified at least one lead to said lead integrity testing circuit for lead integrity testing.

50. The implantable cardiac stimulating device of claim 49, wherein to evaluate the impedances of said plurality of electrical leads, said lead integrity testing circuit applies said low energy test pulse through each of said identified at least one lead in response to said lead integrity test control signal.

51. The implantable cardiac stimulating device of claim 50, wherein said lead integrity testing circuit applies a different low energy test pulse through each of said identified at least one lead in response to said lead integrity test control signal.

52. The implantable cardiac stimulating device of claim 51, wherein said low energy test pulse comprises a pulse width, said implantable cardiac stimulating device further comprising means for selecting the pulse width uniquely for the low energy test pulse associated with each electrical lead.

53. The implantable cardiac stimulating device of claim 51, wherein said low energy test pulse comprises a pulse amplitude, said implantable cardiac stimulating device further comprising means for selecting the pulse amplitude uniquely for the low energy test pulse associated with each electrical lead.

54. The implantable cardiac stimulating device of claim 53, wherein said low energy test pulse comprises a pulse width, said implantable cardiac stimulating device further comprising means for selecting the pulse width uniquely for the low energy test pulse associated with each electrical lead.

55. The implantable cardiac stimulating device of claim 49, wherein said control circuitry further comprises:
    means for selecting a sequence of therapies, wherein each therapy comprises a selection of at least one lead of said plurality of electrical leads; and
    memory means for storing said selected sequence of therapies.

56. The implantable cardiac stimulating device of claim 55, wherein said control circuitry further comprises control means for modifying said stored selected sequence of therapies in response to said results from said lead integrity test.

57. The implantable cardiac stimulating device of claim 43, wherein said control circuitry initiates said lead integrity test independently of delivery of said high energy shock.

58. The implantable cardiac stimulating device of claim 43, wherein said lead integrity testing circuit compares the impedance of said lead to a reference impedance.

59. The implantable cardiac stimulating device of claim 58, wherein said lead integrity testing circuit provides a logic signal to said control circuitry when lead integrity has been compromised.

60. The implantable cardiac stimulating device of claim 43, wherein said low energy test pulse comprises a pulse width, said implantable cardiac stimulating device further comprising means for selecting the pulse width of said low energy test pulse.

61. The implantable cardiac stimulating device of claim 43, wherein said low energy test pulse comprises a pulse amplitude, said implantable cardiac stimulating device further comprising means for selecting the pulse amplitude of said low energy test pulse.

62. The implantable cardiac stimulating device of claim 61, wherein said low energy test pulse comprises a pulse width, said implantable cardiac stimulating device further comprising means for selecting the pulse width of said low energy test pulse.

63. The implantable cardiac stimulating device of claim 43, wherein said low voltage control circuitry initiates lead integrity tests at predetermined intervals.

64. The implantable cardiac stimulating device of claim 63, further comprising means for selecting said predetermined intervals.

65. The implantable cardiac stimulating device of claim 43, said control circuitry further comprising means for detecting refractory periods of said cardiac tissue, wherein said control circuitry initiates lead integrity tests only during said refractory periods.

66. The implantable cardiac stimulating device of claim 65, wherein said control circuitry initiates lead integrity tests at predetermined intervals.

67. The implantable cardiac stimulating device of claim 66, further comprising means for selecting said predetermined intervals.

68. In an implantable cardiac stimulating device detachably coupled to a lead in contact with cardiac tissue, the implantable cardiac stimulating device including:
    high voltage shock delivery circuitry, electrically coupled to said lead, for generating high energy shocks and for delivering said high energy shocks to cardiac tissue through said lead,
    control circuitry for detecting the onset of cardiac arrhythmias and for causing said high voltage shock delivery circuitry to generate and deliver said high energy shocks in response to a detected cardiac arrhythmias,
    means for detecting refractory periods of said cardiac tissue,
    means for evaluating the integrity of said lead and for generating test results, and
    a means for passing signals between said high voltage shock delivery circuit and said control circuitry,
    a method for evaluating the integrity of said lead comprising the steps of:
        generating a lead integrity test control signal, said lead integrity test control signal being generated only when a refractory period of said cardiac tissue is detected by said means for detecting refractory periods;
        generating a test pulse with said high voltage shock delivery circuitry;
        applying said test pulse to said lead in response to said lead integrity test control signal provided by said low voltage control circuitry;
        evaluating the integrity of said lead while said test pulse is being applied;
        generating test results indicative of whether lead integrity has been compromised; and
        providing said test results to said control circuitry.

69. An implantable cardiac stimulating device for administering electrical stimulation to cardiac tissue, said cardiac tissue having periods of refractoriness, through at least one lead to interrupt cardiac arrhythmias, the implantable cardiac stimulating device comprising:
    shock delivery circuitry, electrically coupled to said at least one lead, for generating a high energy shock and for delivering said high energy shock to cardiac tissue through said at least one lead in response to a shock delivery control signal;
    control circuitry for detecting the onset of a cardiac arrhythmia, for detecting refractory periods of said cardiac tissue, for generating said shock delivery control signal to cause said shock delivery circuitry to generate and deliver said high energy shock, and for generating a lead integrity test control signal to initiate a lead integrity test on said at least one lead, wherein said control circuitry initiates lead integrity tests only during said refractory periods;

a lead integrity testing circuit, coupled to said at least one lead, for performing said lead integrity test in response to said lead integrity test control signal and for providing results of said lead integrity test to said control circuitry, wherein the result of said lead integrity test comprises a pass/fail indication of the integrity of said at least one lead;

a means for passing signals between said lead integrity testing circuit and said control circuitry; and a means for passing signals between said shock delivery circuit and said control circuitry.

70. In an implantable cardiac stimulating device detachably coupled to a lead in contact with cardiac tissue, the implantable cardiac stimulating device including:

high voltage shock delivery circuitry, electrically coupled to said lead, for generating high energy shocks and for delivering said high energy shocks to cardiac tissue through said lead, said high voltage shock delivery circuitry coupled to at least one high voltage capacitor for generating said high energy shocks, control circuitry for detecting the onset of cardiac arrhythmias and for causing said high voltage shock delivery circuitry to generate and deliver said high energy shocks in response to a detected cardiac arrhythmias, means for evaluating the integrity of said lead and for generating test results, and a means for passing signals between said high voltage shock delivery circuit and said control circuitry, a method for evaluating the integrity of said lead comprising the steps of:

generating a lead integrity test control signal;

generating a test pulse with said high voltage shock delivery circuitry, said test pulse generated independently of said at least one high voltage capacitor;

applying said test pulse to said lead in response to said lead integrity test control signal provided by said low voltage control circuitry;

evaluating the integrity of said lead while said test pulse is being applied;

generating test results indicative of whether lead integrity has been compromised; and providing said test results to said control circuitry.

71. An implantable cardiac stimulating device for administering electrical stimulation to cardiac tissue, said cardiac tissue having periods of refractoriness, through at least one lead to interrupt cardiac arrhythmias, the implantable cardiac stimulating device comprising:

shock delivery circuitry, electrically coupled to said at least one lead, for generating a high energy shock and for delivering said high energy shock to cardiac tissue through said at least one lead in response to a shock delivery control signal, wherein said shock delivery circuitry comprises at least one high voltage capacitor for generating said high energy shock;

control circuitry for detecting the onset of a cardiac arrhythmia, for generating said shock delivery control signal to cause said shock delivery circuitry to generate and deliver said high energy shock, and for generating a lead integrity test control signal to initiate a lead integrity test on said at least one lead;

a lead integrity testing circuit, coupled to said at least one lead, for performing said lead integrity test in response to said lead integrity test control signal and for providing results of said lead integrity test to said control circuitry, wherein the result of said lead integrity test comprises a pass/fail indication of the integrity of said at least one lead and wherein said lead integrity test is performed independently of said at least one high voltage capacitor;

a means for passing signals between said lead integrity testing circuit and said control circuitry; and a means for passing signals between said shock delivery circuit and said control circuitry.

72. An implantable cardiac stimulating device for administering electrical stimulation to cardiac tissue through at least one lead, the implantable cardiac stimulating device comprising:

means for detecting refractory periods of said cardiac tissue; and means for performing a lead integrity test on said at least one lead, wherein said lead integrity test is initiated only during detected refractory periods of said cardiac tissue.

73. The implantable cardiac stimulating device of claim 72, further comprising means for storing results of said lead integrity test.

74. The implantable cardiac stimulating device of claim 72, further comprising means for communicating results of said lead integrity test to an external programming unit.

75. The implantable cardiac stimulating device of claim 72, wherein said means for performing is electrically coupled to said lead, and said means for performing comprises means for applying a test pulse to said at least one lead.

76. The implantable cardiac stimulating device of claim 75, wherein said test pulse comprises a pulse width, said implantable cardiac stimulating device further comprising means for selecting the pulse width of said test pulse.

77. The implantable cardiac stimulating device of claim 75, wherein said test pulse comprises a pulse amplitude, said implantable cardiac stimulating device further comprising means for selecting the pulse amplitude of said test pulse.

78. The implantable cardiac stimulating device of claim 72, wherein said means for performing initiates lead integrity tests at predetermined intervals.

79. The implantable cardiac stimulating device of claim 78, further comprising means for selecting said predetermined intervals.

\* \* \* \* \*